(12) United States Patent
Garcia-Bengochea et al.

(10) Patent No.: US 9,433,447 B2
(45) Date of Patent: Sep. 6, 2016

(54) INSTRUMENTATION FOR SPINAL FIXATION USING MINIMALLY INVASIVE SURGICAL TECHNIQUES

(71) Applicants: Javier Garcia-Bengochea, Jacksonville, FL (US); Andrew F. Cannestra, Jacksonville, FL (US)

(72) Inventors: Javier Garcia-Bengochea, Jacksonville, FL (US); Andrew F. Cannestra, Jacksonville, FL (US)

( * ) Notice: Subject to any disclaimer, the term of this patent is extended or adjusted under 35 U.S.C. 154(b) by 32 days.

(21) Appl. No.: 14/029,147

(22) Filed: Sep. 17, 2013

(65) Prior Publication Data

US 2014/0018868 A1    Jan. 16, 2014

Related U.S. Application Data

(63) Continuation of application No. 12/931,953, filed on Feb. 14, 2011, now Pat. No. 8,540,720, which is a continuation-in-part of application No. 12/315,546, filed on Dec. 4, 2008, now abandoned.

(60) Provisional application No. 61/005,523, filed on Dec. 6, 2007.

(51) Int. Cl.
*A61B 17/70* (2006.01)
*A61B 17/88* (2006.01)

(52) U.S. Cl.
CPC ....... *A61B 17/7089* (2013.01); *A61B 17/7085* (2013.01); *A61B 17/8897* (2013.01)

(58) Field of Classification Search
CPC ................ A61B 17/8897; A61B 2017/90
USPC ....... 606/246, 279, 86 A, 86 R, 99, 103–105
See application file for complete search history.

(56) References Cited

U.S. PATENT DOCUMENTS

| | | | |
|---|---|---|---|
| 6,821,277 B2 | 11/2004 | Teitelbaum | |
| 7,056,321 B2 | 6/2006 | Pagliuca et al. | |
| 7,179,261 B2 | 2/2007 | Sicvol et al. | |
| 7,188,626 B2 | 3/2007 | Foley et al. | |
| 7,250,052 B2 | 7/2007 | Landry et al. | |
| 7,648,521 B2 * | 1/2010 | Hestad | 606/246 |
| 7,758,617 B2 | 7/2010 | Lott et al. | |
| 7,857,813 B2 * | 12/2010 | Schmitz et al. | 606/79 |
| 8,038,699 B2 | 10/2011 | Cohen et al. | |
| 8,043,343 B2 * | 10/2011 | Miller et al. | 606/279 |
| 2002/0082598 A1 | 6/2002 | Teitelbaum | |
| 2005/0080418 A1 * | 4/2005 | Simonson et al. | 606/61 |
| 2005/0277934 A1 * | 12/2005 | Vardiman | 606/61 |
| 2007/0123888 A1 * | 5/2007 | Bleich et al. | 606/79 |
| 2007/0299444 A1 * | 12/2007 | DiPoto et al. | 606/61 |
| 2008/0015582 A1 * | 1/2008 | DiPoto et al. | 606/61 |
| 2008/0140120 A1 * | 6/2008 | Hestad et al. | 606/246 |
| 2008/0275458 A1 | 11/2008 | Bleich et al. | |
| 2009/0171391 A1 * | 7/2009 | Hutton et al. | 606/246 |
| 2010/0004701 A1 * | 1/2010 | Malandain et al. | 606/86 R |
| 2010/0087828 A1 | 4/2010 | Krueger et al. | |

* cited by examiner

*Primary Examiner* — Jan Christopher Merene
*Assistant Examiner* — Steven Cotroneo
(74) *Attorney, Agent, or Firm* — Thomas C. Saitta

(57) ABSTRACT

A cable threader device for passing a guide cable between pedicle screws during minimally invasive spinal surgery, the device comprising a handle with a trigger mechanism, the handle mounted onto an elongated shaft having a curved free end with a detachable curved lead member retained in telescoping manner on the end of the body. The guide cable is affixed to the lead member, the instrument is inserted into a first screw tower, the trigger mechanism is activated to advance the lead member into the adjacent tower, and the lead member and guide cable are retrieved through the second tower.

8 Claims, 2 Drawing Sheets

INSTRUMENTATION FOR SPINAL FIXATION USING MINIMALLY INVASIVE SURGICAL TECHNIQUES

This application is a continuation of U.S. patent application Ser. No. 12/931,953, filed Feb. 14, 2011, now allowed, which is a continuation-in-part of U.S. patent application Ser. No. 12/315,546, filed Dec. 4, 2008, claiming the benefit of U.S. Provisional Patent Application Ser. No. 61/005,523, filed Dec. 4, 2007, the disclosures of all of which are incorporated herein by reference.

BACKGROUND OF THE INVENTION

This invention relates generally to the field of systems, instrumentation and methodology for the fixation of vertebrae relative to each other, and more particularly relates to such systems, instrumentation and methodology that utilize pedicle screws affixed to vertebral pedicles and one or more rods that rigidly join the pedicle screws of plural vertebrae. The invention contemplates the combination and use of plural pedicle screws, one or more rods and means to optimize insertion of the rod into the pedicle screws, such means comprising a guide cable and instrumentation to position the guide cable in the pedicle screws, whereby the screws are implanted into the vertebrae, the guide cable positioned in the screws and the rod subsequently guided into the pedicle screws along the guide cable, all using minimally invasive surgical incisions. With regard to instrumentation of the invention, the invention relates to guide cable threading or advancing devices adapted to pass the guide cable from one pedicle screw to an adjacent pedicle screw.

Early surgical techniques for affixing rods to vertebrae entailed relatively long incisions to provide access to the vertebrae. Newer techniques utilize multiple percutaneous stab incisions at chosen locations rather than a single long incision. Such techniques are often referred to as minimally invasive surgery (MIS). The MIS techniques are preferable with regard to recovery time.

One advanced MIS technique provides for the placement and passing of a guide cable or wire between the pedicle screws such that the guide cable can be utilized to direct and/or pull a fixation rod into proper position spanning the pedicle screws. Inserting and passing the guide cable through the tissue between the pedicle screws can be a difficult and time-consuming task. It is an object of this invention therefore to provide an instrument that greatly reduces the difficulty in this task.

SUMMARY OF THE INVENTION

The invention comprises in general an instrument and method of using the instrument in conjunction with the combination and use of plural pedicle screws implanted into vertebrae, screw extenders or towers extending from the pedicle screws to provide access to the heads of the screws, one or more rods for connecting the pedicle screws in a relatively rigid manner to prevent undesirable movement of the vertebrae, wherein a guide cable is inserted and positioned between the heads of the pedicle screws to guide the rod into proper position bridging the pedicle screws, all using minimally invasive surgical incisions. The instrument is a cable threader device, the device comprising a handle with a trigger mechanism, the handle mounted onto an elongated shaft having a curved free end with a detachable curved lead member retained in telescoping manner on the end of the shaft, the lead member having means to receive or connect the guide cable thereto. With this structure, the guide cable is attached to the lead member and the free end of the instrument is inserted into one of the screw towers facing the adjacent screw tower, such that when the trigger is actuated the lead member is extended to and into the adjacent screw tower, where the lead member can be grasped and pulled from the tower to advance the guide cable. The instrument is then removed form the first tower, the lead member is reattached to the elongated shaft and reinserted into the tower so as to face the next tower. The steps are repeated until the guide cable has been passed through all the pedicle screws.

In an alternative embodiment, the lead member is non-detachable from the free end and comprises a hollow sleeve open at both ends, such that when the lead member is advanced the combination of the curved free end and the lead member defines a tunnel though which the guide cable is pushed, the end of the guide cable or a loop of the guide cable if it is doubled back on itself then passing directly into the second pedicle screw tower, where it can be grasped and pulled out of the patient's body.

DETAILED DESCRIPTION OF THE INVENTION

Figure 1:
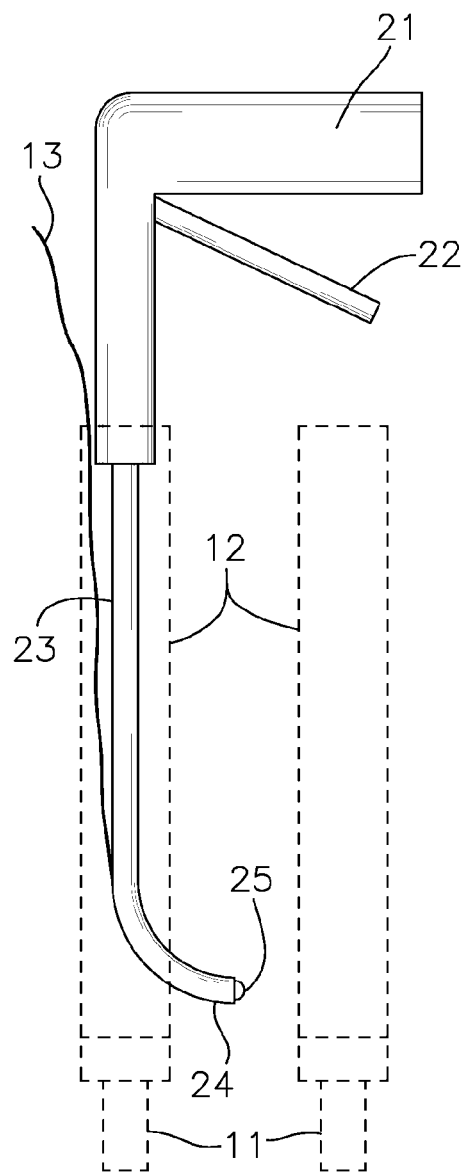
FIG. 1 illustrates a side view of the cable threader instrument showing the instrument inserted into a first screw tower.
Figure 2:
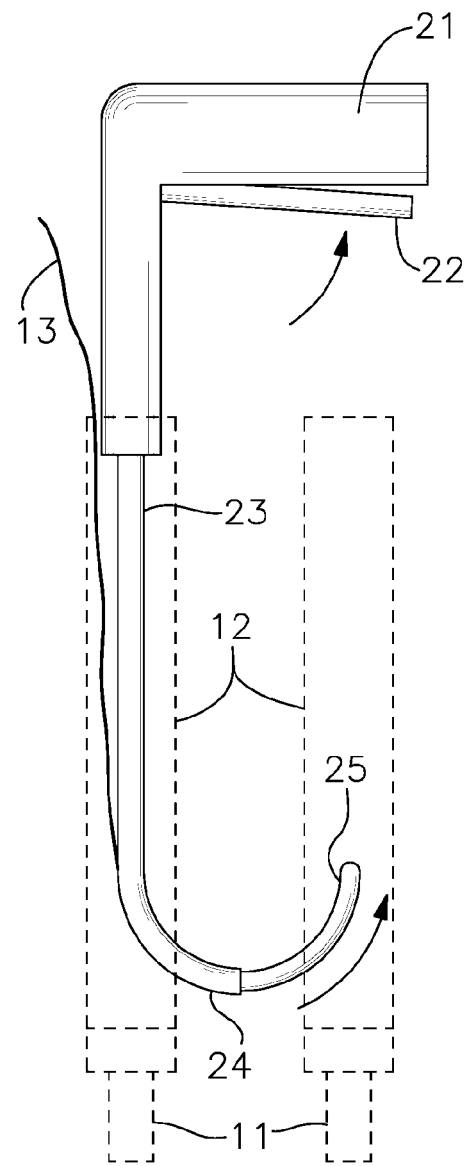
FIG. 2 is a side view similar to FIG. 1 showing the lead member advanced into an adjacent screw tower.
Figure 3:
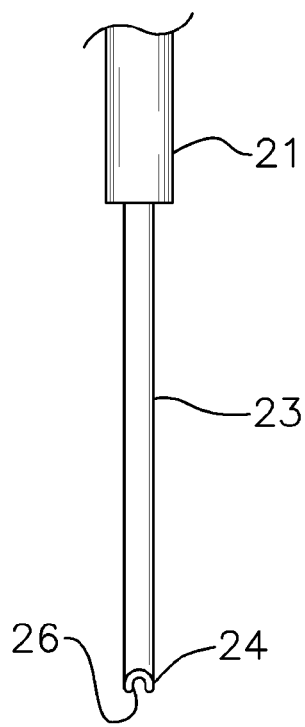
FIG. 3 is a front view of the instrument showing the guide cable receiving channel.
Figure 4:
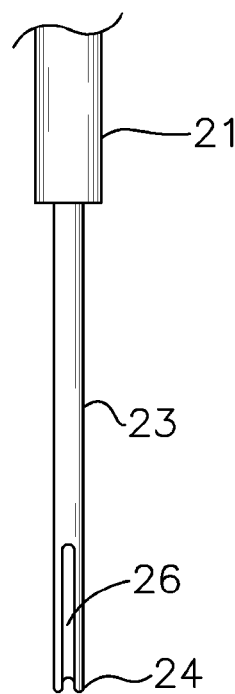
FIG. 4 is a rear view of the instrument showing the guide cable receiving channel
Figure 5:
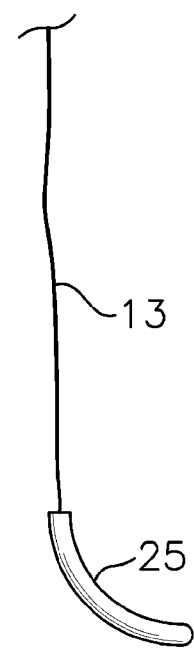
FIG. 5 is a side view showing the guide cable connected to the detachable lead member.

With reference to the drawings the invention will now be described in detail with regard for the best mode and the preferred embodiment. The invention comprises in general an instrument and method of using the instrument in conjunction with the combination and use of plural pedicle screws 11 implanted into vertebrae, screw extenders or towers 12 extending from the pedicle screws 11 to provide access to the heads of the screws 11, one or more rods for connecting the pedicle screws 11 in a relatively rigid manner to prevent undesirable movement of the vertebrae, wherein a guide cable or wire 13 is inserted and positioned between the heads of the pedicle screws 11 to guide the rod into proper position bridging the pedicle screws 11, all using minimally invasive surgical incisions.

Pedicle fixation is accomplished by creating multiple percutaneous incisions, as opposed to an open or long incision, often referred to as stab incisions. The percutaneous incisions allow for pedicle screws 11 to be inserted into each desired vertebra by cutting or making a short incision, drilling into the vertebra and inserting a pedicle screw 11. Screw extenders or towers 12 are connected to the pedicle screws 11 the towers 12 having slotted sides to provide access to their interiors. The guided cable 13, preferably a braided member composed of stainless steel or titanium, is either attached directly to the head of the first or outermost of the pedicle screws 11 or the free end is allowed to remain outside of the patient.

The instrument used to manipulate the guide cable 13 is a cable threader device, the device comprising a handle 21 with a trigger mechanism 22, the handle 21 mounted onto an elongated shaft 23 having a curved free end 24 having an inner diameter, with a detachable curved lead member 25 retained in telescoping manner on the end of the shaft 23, the lead member 25 having a rounded nose and means for connecting the guide cable 13 thereto, such as a hook or other mechanical fastening mechanism, the lead member 25 having an outer diameter of slightly lesser diameter than the inner diameter of the curved free end and of greater diameter than the outer diameter of the guide cable 13. Preferably the handle 21 and shaft 23 are rotatably joined. The combination of free end 24 and elongated shaft 23 define a general J-shape. The curved free end 24 of the instrument is provided with a cable slot 26 to temporarily receive the guide cable 13. With this structure, the guide cable 13 is attached to the lead member 25 and the free end 24 of the instrument is inserted into one of the screw towers 12 facing the adjacent screw tower 12, such that when the trigger mechanism 22 is actuated the lead member 25 is extended through the intervening tissue and into the adjacent screw tower 12, where the lead member 25 can be grasped using forceps or similar devices and pulled from the tower 12 to advance the guide cable 13. The trigger mechanism 22 may comprise any suitable known arrangement of elements, such as a relatively rigid cable or rod advanced downwardly in the shaft 23 by compression of the trigger mechanism 22. The instrument is then removed from the first tower 12, the intermediate portion of the guide wire 13 is separated from the instrument, and the lead member 25 is reattached to the elongated shaft 23 and reinserted into the tower 12 so as to face the next tower 12. The steps are repeated until the guide cable 13 has been passed through all the pedicle screws 11.

Figure 6:
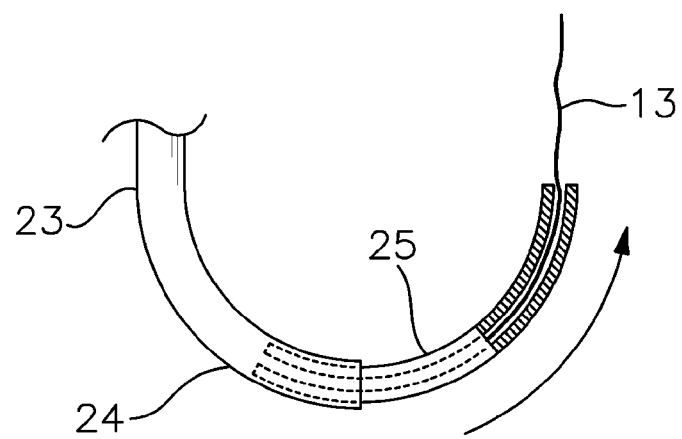
FIG. 6 is a side view showing an alternative embodiment of the lead member, shown partially in cross-section, wherein the lead member is a hollow sleeve.

In an alternate embodiment depicted in FIG. 6, the lead member 25 comprises a hollow sleeve open at both ends, such that when the lead member 25 is advanced the combination of the curved free end 24 and the lead member 25 defines a tunnel though which the guide cable 13 is pushed, the end of the guide cable 13 or a loop of the guide cable 13 if it is doubled back on itself then passing directly into the second pedicle screw tower 25, where it can be grasped and pulled out of the patient's body. The instrument is then removed from the first tower 25 and from the guide cable 13, and the free end or loop of the guide cable 13 extending from the second tower 25 is then reinserted into the instrument and the process is repeated.

Once the cable 13 has been properly positioned in the heads of the pedicle screws 11, it is finally brought out through a percutaneous incision at an offset or displaced location. A cannulated or tubular rod is then inserted over the free end of the cable 13 and passed down the cable 13 through the offset incision using a rod insertion instrument. The rod is preferably malleable in vivo to account for torque imparted by the set screws used to secure the rod to the pedicle screws 11. After the rod is properly positioned, the rod is affixed or secured to the pedicle screws 11 in standard manner, the cable 13 is cut or withdraw and the screw towers 12 are removed.

It is understood that equivalents and substitutions for elements set forth above may be obvious to those of ordinary skill in the art, and therefore the true scope and definition of the invention is to be as set forth in the following claims.

We claim:

1. A guide cable threader device adapted to advance a guide cable from one pedicle screw tower to another pedicle screw tower, said device comprising:

a handle, a trigger mechanism disposed in said handle, an elongated J-shaped shaft extending from said handle, said elongated shaft having a linear portion and a non-linear, curved free end having an inner diameter, said curved free end comprising an elongated slot receiving a guide cable therethrough, said guide cable being disposed externally to said linear portion of said elongated shaft and internally to said curved free end of said elongated shaft, said guide cable having an outer diameter, and a non-linear, curved lead member telescopically disposed within said curved free end of said elongated shaft, said lead member connected to said guide cable, said lead member having an outer diameter greater than the outer diameter of said guide cable and slightly lesser than the inner diameter of said curved free end, whereby said lead member is extended from said curved free end of said elongated shaft upon actuation of said trigger mechanism such that said guide cable is advanced through said elongated slot and such that said lead member and said guide cable may be pulled completely from said curved free end to separate said guide cable and said lead member from said elongated shaft.

2. The device of claim 1, wherein said handle and said elongated shaft are rotatably joined.

3. The device of claim 1, wherein the curvature of said lead member matches the curvature of said free end of said shaft.

4. The device of claim 1, wherein said lead member is detachable connected to said guide cable.

5. A guide cable threader device adapted to advance a guide cable from one pedicle screw tower to another pedicle screw tower, said device comprising:

a handle, a trigger mechanism disposed in said handle, an elongated J-shaped shaft extending from said handle, said elongated shaft having a linear portion and a non-linear, curved free end having an inner diameter, said curved free end comprising an elongated slot adapted to receive a guide cable therethrough, said guide cable being disposed externally to said linear portion of said elongated shaft and internally to said curved free end of said elongated shaft, said guide cable having an outer diameter, and a non-linear, curved lead member telescopically disposed within said curved free end of said elongated shaft, said lead member connected to said guide cable, said lead member having an outer diameter greater than the outer diameter of said guide cable and slightly lesser than the inner diameter of said curved free end, whereby said lead member is extended from said curved free end of said elongated shaft upon actuation of said trigger mechanism such that said guide cable is advanced through said elongated slot and such that said lead member and said guide cable may be pulled completely from said curved free end to separate said guide cable and said lead member from said elongated shaft.

6. The device of claim 5, wherein said handle and said elongated shaft are rotatably joined.

7. The device of claim 5, wherein the curvature of said lead member matches the curvature of said free end of said shaft.

8. The device of claim 5, wherein said lead member is detachable connected to said guide cable.

* * * * *